United States Patent [19]

Rawlinson et al.

[11] Patent Number: 5,728,889
[45] Date of Patent: Mar. 17, 1998

[54] PROCESS FOR THE PRODUCTION OF 2-(SUBSTITUTED BENZOYL)-1,3 CYCLOHEXANEDIONES

[75] Inventors: Howard Rawlinson, Sowery Bridge; Jonathan William Wiffen, Rodley; Stephen Martin Brown, Upper Cumberworth, all of United Kingdom

[73] Assignee: Zeneca Limited, London, England

[21] Appl. No.: 860,334

[22] PCT Filed: Jan. 16, 1996

[86] PCT No.: PCT/GB96/00081

§ 371 Date: Jun. 24, 1997

§ 102(e) Date: Jun. 24, 1997

[87] PCT Pub. No.: WO96/22957

PCT Pub. Date: Aug. 1, 1996

[30] Foreign Application Priority Data

Jan. 25, 1995 [GB] United Kingdom .................. 9501433

[51] Int. Cl.⁶ .................. C07C 49/23; C07C 49/213
[52] U.S. Cl. .................. 568/329; 568/308
[58] Field of Search .................. 568/308, 329, 568/331, 335, 351, 376

[56] References Cited

U.S. PATENT DOCUMENTS

| | | | |
|---|---|---|---|
| 4,695,673 | 9/1987 | Heather et al. | 568/310 |
| 4,774,360 | 9/1988 | Bay . | |
| 4,780,127 | 10/1988 | Michaely et al. | 71/103 |
| 4,806,146 | 2/1989 | Carter | 71/98 |
| 4,837,352 | 6/1989 | Knudsen . | |
| 4,937,386 | 6/1990 | Ueda et al. . | |
| 4,946,981 | 8/1990 | Carter et al. | 558/415 |
| 5,006,158 | 4/1991 | Carter et al. | 71/98 |
| 5,089,046 | 2/1992 | Lee et al. . | |
| 5,248,683 | 9/1993 | Brunner et al. . | |
| 5,468,878 | 11/1995 | Nasuno et al. | 549/23 |
| 5,480,858 | 1/1996 | Sakamoto et al. | 504/288 |

*Primary Examiner*—Gary Geist
*Assistant Examiner*—Karl J. Puttlitz, Jr.
*Attorney, Agent, or Firm*—Joseph R. Snyder

[57] ABSTRACT

A process for preparing a compound of formula (I), where $R^1$, $R^2$, $R^3$, $R^4$, $R^5$ and $R^6$ are independently hydrogen or $C_{1-6}$ alkyl; $R^7$ is halogen, cyano, $NO_2$, $C_{1-4}$ alkyl, $C_{1-4}$ haloalkyl, $C_{1-4}$ alkoxy or RaS in which Ra is $C_{1-4}$ alkyl; $R^8$, $R^9$ and $R^{10}$ independently are hydrogen, halogen, $C_{1-4}$ alkyl, $C_{1-4}$ alkoxy, $C_{1-4}$ haloalkyl, $C_{1-4}$ haloalkoxy, CN, $NO_2$, phenoxy or substituted phenoxy; $R_bS(O)n$ Om in which m is 0 or 1, n is 0, 1 or 2 and Rb is $C_{1-4}$ alkyl, $C_{1-4}$ haloalkyl, phenyl or benzyl, $NHCOR_c$ in which c is $C_{1-4}$ alkyl, NRdRe in which Rd and Re independently are hydrogen or $C_{1-4}$ alkyl; RfC(O)— in which Rf is hydrogen, $C_{1-4}$ alkyl, $C_{1-4}$ haloalkyl or $C_{1-4}$ alkoxy; $SO_2NRgRh$ in which Rg and Rh independently are hydrogen or $C_{1-4}$ alkyl; or any two of $R^8$, $R^9$ and $R^{10}$ together with the carbon atoms to which they are attached form a 5 or 6 membered heterocyclic ring containing up to three heteroatoms selected from 0, N or S and which may be optionally substituted by $C_{1-4}$ alkyl, $C_{1-4}$ haloalkyl, $C_{1-4}$ alkoxy, $=NOC_{1-4}$ alkyl, or halogen; which process comprises the rearrangement of a compound of formula (II), where $R^1$, $R^2$, $R^3$, $R^4$, $R^5$, $R^6$, $R^7$, $R^8$, $R^9$ and $R^{10}$ are as defined in relation to formula (I), in the presence of a base and a polar aprotic solvent characterized in that the process is carried out in a reaction medium substantially free of hydrogen cyanide or cyanide anion.

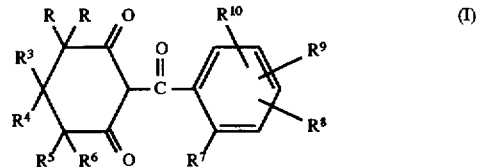

(I)

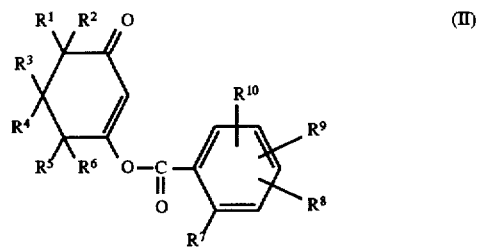

(II)

9 Claims, No Drawings

PROCESS FOR THE PRODUCTION OF 2-(SUBSTITUTED BENZOYL)-1,3 CYCLOHEXANEDIONES

The present invention relates to the production of 2-(substituted benzoyl)-1,3-cyclohexanedione compounds.

2-(substituted benzoyl)-1,3-cyclohexanediones are known as herbicides from for example U.S. Pat. No. 4,780, 127, U.S. Pat. No. 4,806,146, U.S. Pat. No. 4,946,981, U.S. Pat. No. 5,006,158, WO 9408988 and WO 9404524. One method of producing these compounds is by re-arrangement of an enol ester. This method is described in U.S. Pat No. 4,780,127 and U.S. Pat. No. 4,695,673. In these rearrangement reactions the presence of hydrogen cyanide or cyanide anion is described as essential (generally in an amount of 1-10 mol percent with respect to the enol ester). In an industrial scale process it is desirable to avoid the use of such materials. Surprisingly it has now been found that in certain solvents it is possible to perform the rearrangement in the absence of hydrogen cyanide or cyanide anion.

According to the present invention there is provided a process for preparing a compound of formula (I) where $R^1$, $R^2$, $R^3$, $R^4$, $R^5$ and $R^6$ are independently hydrogen or $C_{1-6}$ alkyl; $R^7$ is halogen, cyano, $NO_2$, $C_{1-4}$ alkyl, $C_{1-4}$ haloalkyl, $C_{1-4}$ alkoxy or RaS in which Ra is $C_{1-4}$ alkyl; $R^8$, $R^9$ and $R^{10}$ independently are hydrogen, halogen, $C_{1-4}$ alkyl, $C_{1-4}$ alkoxy, $C_{1-4}$ haloalkyl, $C_{1-4}$ haloalkyl, CN, $NO_2$, phenoxy or substituted phenoxy; $R_bS(O)nOm$ in which m is 0 or 1, n is 0, 1 or 2 and Rb is $C_{1-4}$ alkyl, $C_{1-4}$ haloalkyl, phenyl or benzyl, $NHCOR_c$ in which Rc is $C_{1-4}$ alkyl, NRdRe in which Rd and Re are independently hydrogen or $C_{1-4}$ alkyl; RfC(O)— in which Rf is hydrogen, $C_{1-4}$ alkyl, $C_{1-4}$ haloalkyl or $C_{1-4}$ alkoxy; $SO_2NRgRh$ in which Rg and Rh independently are hydrogen or $C_{1-4}$ alkyl; or any two of $R^8$, $R^9$ and $R^{10}$ together with the carbon atoms to which they are attached form a 5 or 6 membered heterocyclic ring containing up to three heteroatoms selected from O, N or S and which may be optionally substituted by $C_{1-4}$ alkyl, $C_{1-4}$ haloalkyl, $C_{1-4}$ alkoxy, $=NOC_{1-4}$ alkyl or halogen; which process comprises the rearrangement of a compound of formula (II) where $R^1$, $R^2$, $R^3$, $R^4$, $R^5$, $R^6$, $R^7$, $R^8$, $R^9$ and $R^{10}$ are as defined in relation to formula (I), in the presence of a base and a polar aprotic solvent characterised in that the process is carried out in a reaction medium substantially free of hydrogen cyanide or cyanide anion.

As used herein the term "alkyl", refers to straight or branched chains. The term "haloalkyl" refers to an alkyl group substituted by at least one halogen. Similarly the term "haloalkoxy" refers to an alkoxy group substituted by at least one halogen. As used herein the term "halogen" refers to fluorine, chlorine, bromine and iodine.

Suitable optional substituents for phenoxy groups $R^8$, $R^9$ and $R^{10}$ include halogen such as fluorine and chlorine and $C_{1-4}$ haloalkyl.

A preferred group of compounds of formula (I) are those where $R^1$, $R^2$, $R^3$, $R^4$, $R^5$ and $R^6$ are independently hydrogen or $C_{1-6}$ alkyl; $R^7$ is halogen, cyano, $NO_2$, $C_{1-4}$ alkyl, $C_{1-4}$ haloalkyl, $C_{1-4}$ alkoxy or RaS in which Ra is $C_{1-4}$ alkyl; $R^8$, $R^9$ and $R^{10}$ independently are hydrogen, halogen, $C_{1-4}$ alkyl, $C_{1-4}$ alkoxy, $C_{1-4}$ haloalkyl, $C_{1-4}$ haloalkoxy, CN, $NO_2$, phenoxy or substituted phenoxy; $R_bS(O)nOm$ in which m is 0 or 1, n is 0, 1 or 2 and Rb is $C_{1-4}$ alkyl, $C_{1-4}$ haloalkyl, phenyl or benzyl, $NHCOR_c$ in which Rc is $C_{1-4}$ alkyl, NRdRe in which Rd and Re independently are hydrogen or $C_{1-4}$ alkyl; RfC(O)— in which Rf is hydrogen, $C_{1-4}$ alkyl, $C_{1-4}$ haloalkyl or $C_{1-4}$ alkoxy; or $SO_2NRgRh$ in which Rg and Rh independently are hydrogen or $C_{1-4}$ alkyl.

Preferably $R^1$, $R^2$, $R^3$, $R^4$, $R^5$ and $R^6$ are independently hydrogen or $C_{1-4}$ alkyl. More preferably $R^1$, $R^2$, $R^5$ and $R^6$ are hydrogen and $R^3$ and $R^4$ are independently hydrogen or methyl.

$R^7$ is preferably halogen or $NO_2$. A preferred value for $R^8$ is hydrogen.

$R^9$ is preferably hydrogen or $C_{1-4}$ alkoxy, especially ethoxy. Most preferably $R^9$ is hydrogen.

Preferably $R^{10}$ is a group $RbS(O)nOm$ where Rb, n and m are as defined above. More preferably m is zero, n is 2 and Rb is $CH_3$ or $C_2H_5$. Most preferably $R^{10}$ is a group $CH_3SO_2$ attached to the benzoyl group at the 4-position.

Suitable bases include both organic bases such as trialkylamines and inorganic bases such as alkali metal carbonates and phosphates. The trialkylamines are preferably tri(lower alkyl)amines having from 1 to 6, preferably 1 to 4 carbon atoms per alkyl group. A particularly preferable amine is triethylamine. Suitable inorganic bases include sodium carbonate, potassium carbonate and trisodium phosphate. Even a bicarbonate such as potassium bicarbonate will function effectively in this reaction when used in combination with a dipolar aprotic solvent such as dimethylformamide. Preferred bases are sodium carbonate and potassium carbonate.

The base is used in an amount of from about 1 to about 4 moles per mole of enol ester, preferably about 2 moles per mole.

As used herein the expressions "substantially free of hydrogen cyanide or cyanide anion" means that neither of these moieties is deliberately added to the reaction medium.

Preferred solvents for the process are acetonitrile, dimethylformamide, tetrahydrofuran and mixtures of these solvents with non-polar solvents such as toluene and xylene.

In general, depending on the nature of the reactants, the base and the solvent the rearrangements may be conducted at temperatures from 0° C., up to about 100° C. Preferably the temperature is at a maximum of about 80° C. Most preferably the temperature is from about 20° C., to about 70° C. In some cases, for instance when there is a possible problem of excessive by-product formation (for instance, when using an orthonitro benzoyl halide) the temperature should be kept at about 40° C. maximum.

The process may be carried out using the enol ester as the starting material, or with generation of the enol ester in situ, for instance by reaction of a compound of formula (III) where $R^1$, $R^2$, $R^3$, $R^4$, $R^5$ and $R^6$ are as defined in relation to formula (I) with a compound of formula (IV) where $R^7$, $R^8$, $R^9$ and $R^{10}$ are as defined in relation to formula (I) and Z is a halo, preferably chloro.

When the enol ester is utilised as a starting material it may be prepared by any of a number of known means, including acylation of a compound of formula (III) with, a compound of formula (IV).

The production of compounds of formula (I) according to this invention, may be advantageously carried out starting with compounds of formula (III) and formula (IV) may be carried out with or without isolation of the intermediate enol ester. When carried out in two steps, the compound of formula (III) and the compound of formula (IV) are reacted in the presence of a moderate base such as sodium carbonate or triethylamine. The enol ester isolated from the resulting product mix by known techniques, for instance washing the resultant solution with acid and base, and with saturated sodium chloride solution, and drying. Such a technique is advantageous when a different solvent is preferred for the second step— the rearrangement of the enol ester to the compound of formula (I). The dried enol ester may be mixed with an appropriate solvent such as acetonitrile, or tetrahydrofuran and contacted with the appropriate amounts of moderate base and heated to an temperature, to produce the final product.

Alternatively, the enol ester may be retained in the reaction product and the second stage may be carried out (using the same solvent) by adding additional base if necessary to produce the compound of formula (I).

Comparable yields can be obtained either with or without isolation of the enol ester.

The compound of formula (I) is obtained from this reaction in the form of its salt. The desired acylated compound of formula (I) may be obtained with acidification and extraction with an appropriate solvent.

The process of the invention is illustrated by the following example.

EXAMPLE 1

Acetonitrile (25 g) was charged to a 4 necked 250 ml flamed dried round bottom flask previously purged with $N_2$ and sealed to a Drierite guard tube and oil bubbler. 1,3 cyclohexanedione (5.0 g) and sodium carbonate powder (12.0 g) were charged to give a red slurry. This mass was heated to 55°–57° C. and held for 20 minutes. 2-chloro-4-(methylsulphonyl)benzoyl chloride (11.0 g) was added to acetonitrile (25 g) and warmed gently to obtain a complete solution. This solution was added to the mass dropwise over 20 minutes at 55°–57° C. to give a pale yellow slurry. The mass was held at 55°–57° C. for 17 hours. The required compound of formula (I) as the sodium salt was produced in 82% yield.

EXAMPLE 2

In a second example the acetonitrile in Example 1 was replaced by dimethylformamide and the sodium carbonate was replaced with an equimolar amount of potassium carbonate. Following the same procedures, the reaction was complete 20 minutes after the acid chloride additions was ended and the yield of the required compound of formula (I) as the potassium salt was 54%.

EXAMPLE 3

The procedure of Example 1 was repeated using triethylamine in place of sodium carbonate and DMF in place of acetonitrile. The reaction was complete after 4 hours with a yield of 45%.

CHEMICAL FORMULAE (In Description)

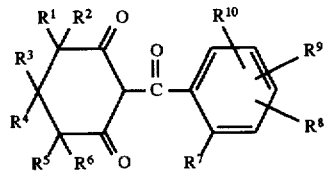

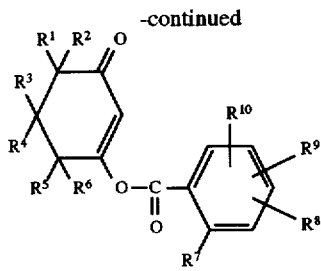

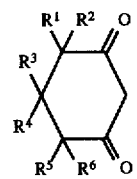

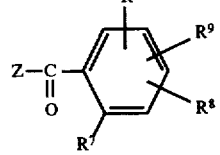

We claim:

1. A process for preparing a compound of formula (I):

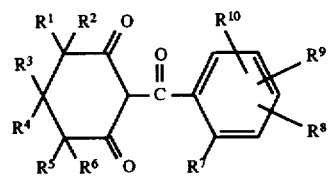

where $R^1$, $R^2$, $R^3$, $R^4$, $R^5$ and $R^6$ are independently hydrogen or $C_{1-6}$ alkyl; $R^7$ is halogen, cyano, $NO_2$, $C_{1-4}$ alkyl, $C_{1-4}$ haloalkyl, $C_{1-4}$ alkoxy or $R_aS$ in which $R_a$ is $C_{1-4}$ alkyl; $R^8$, $R^9$ and $R^{10}$ independently are hydrogen, halogen, $C_{1-4}$ alkyl, $C_{1-4}$ alkoxy, $C_{1-4}$ haloalkyl, $C_{1-4}$ haloalkoxy, CN, $NO_2$, phenoxy or substituted phenoxy; $R_bS(O)n$ Om in which m is 0 or 1, n is 0, 1 or 2 and $R_b$ is $C_{1-4}$ alkyl, $C_{1-4}$ haloalkyl, phenyl or benzyl, $NHCOR_c$ in which $R_c$ is $C_{1-4}$ alkyl, $NRdRe$ in which $R_d$ and $R_e$ independently are hydrogen or $C_{1-4}$ alkyl; $R_fC(O)—$ in which $R_f$ is hydrogen, $C_{1-4}$ alkyl, $C_{1-4}$ haloalkyl or $C_{1-4}$ alkoxy; $SO_2NR_gR_h$ in which $R_g$ and $R_h$ independently are hydrogen or $C_{1-4}$ alkyl; or any two of $R^8$, $R^9$ and $R^{10}$ together with the carbon atoms to which they are attached form a 5 or 6 membered heterocyclic ring containing up to three heteroatoms selected from O, N or S and which may be optionally substituted by $C_{1-4}$ alkyl, $C_{1-4}$ haloalkyl, $C_{1-4}$ alkoxy, $=NOC_{1-4}$ alkyl, or halogen; which process comprises the rearrangement of a compound of formula (II):

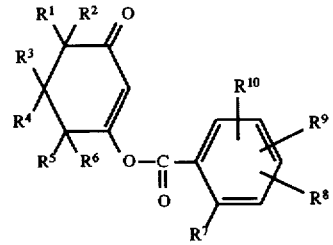

where $R^1$, $R^2$, $R^3$, $R^4$, $R^5$, $R^6$, $R^7$, $R^8$, $R^9$ and $R^{10}$ are as defined in relation to formula (I), in the presence of a base and a polar aprotic solvent characterised in that the process is carried out in a reaction medium substantially free of hydrogen cyanide or cyanide anion.

2. A process according to claim 1 where $R^1$, $R^2$, $R^3$, $R^4$, $R^5$ and $R^6$ are independently hydrogen or $C_{1-6}$ alkyl; $R^7$ is halogen, cyano, $NO_2$, $C_{1-4}$ alkyl, $C_{1-4}$ haloalkyl, $C_{1-4}$ alkoxy or $R_aS$ in which $R_a$ is $C_{1-4}$ alkyl; $R^8$, $R^9$ and $R^{10}$ independently are hydrogen, halogen, $C_{1-4}$ alkyl, $C_{1-4}$ alkoxy, $C_{1-4}$ haloalkyl, $C_{1-4}$ haloalkoxy, CN, $NO_2$, phenoxy or substituted phenoxy; $R_bS(O)n$ $Om$ in which m is 0 or 1, n is 0, 1 or 2 and $R_b$ is $C_{1-4}$ alkyl, $C_{1-4}$ haloalkyl, phenyl or benzyl, $NHCOR_c$ in which $R_c$ is $C_{1-4}$ alkyl, $NR_dR_e$ in which $R_d$ and $R_e$ independently are hydrogen or $C_{1-4}$ alkyl; $R_fC(O)$— in which $R_f$ is hydrogen, $C_{1-4}$ alkyl, $C_{1-4}$ haloalkyl or $C_{1-4}$ alkoxy; or $S_2NR_gR_h$ in which $R_g$ and $R_h$ independently are hydrogen or $C_{1-4}$ alkyl.

3. A process according to claim 1 where $R^1$, $R^2$, $R^5$ and $R^6$ are hydrogen and $R^3$ and $R^4$ are independently hydrogen or methyl.

4. A process according to claim 1 where $R^7$ is halogen or $NO_2$.

5. A process according to claim 1 where $R^8$ is hydrogen.

6. A process according to claim 1 where hydrogen or $C_{1-4}$ alkoxy.

7. A process according to claim 1 where $R^{10}$ is a group $CH_3SO_2$ attached to the benzoyl group at the 4-position.

8. A process according to claim 1 where the solvent is acetonitrile, dimethylformamide, tetrahydrofuran or mixtures of these solvents with toluene or xylene.

9. A process according to claim 1 where the base is triethylamine, sodium carbonate or potassium carbonate.

* * * * *